United States Patent [19]
Bachar

[11] Patent Number: 5,514,324
[45] Date of Patent: May 7, 1996

[54] PREPARATION OF AN ABSORBENT SHEET

[75] Inventor: Moshe Bachar, Kibbutz Amir, Israel

[73] Assignee: Tafnukim Amir Paper Products, Galil Elion, Israel

[21] Appl. No.: 43,579

[22] Filed: Apr. 7, 1993

[30] Foreign Application Priority Data

Mar. 3, 1993 [IL] Israel ......... 104929

[51] Int. Cl.⁶ ................ B27N 3/02; D04H 1/00
[52] U.S. Cl. ............... 264/518; 19/302; 19/304; 264/113; 425/81.1; 425/83.1
[58] Field of Search ............... 425/80.1, 81.1, 425/82.1, 83.1; 604/368; 264/40.7, 112, 113, 121, 518; 156/62.2; 19/302, 304, 145, 296

[56] References Cited

U.S. PATENT DOCUMENTS

| | | | |
|---|---|---|---|
| 2,746,895 | 5/1956 | Duvall | 425/83.1 |
| 3,187,386 | 6/1965 | Schubert et al. | 425/83.1 |
| 3,939,532 | 2/1976 | Wiegand | 425/82.1 |
| 4,264,289 | 4/1981 | Day . | |
| 4,388,056 | 6/1983 | Lee et al. . | |
| 4,543,690 | 10/1985 | Potters | 19/304 |
| 4,688,301 | 8/1987 | Thorbjornsson et al. | 19/304 |
| 4,927,346 | 5/1990 | Kaiser et al. . | |
| 4,927,582 | 5/1990 | Bryson | 264/121 |
| 5,017,324 | 5/1991 | Kaiser et al. . | |
| 5,028,224 | 7/1991 | Pieper et al. | 264/113 |
| 5,102,585 | 4/1992 | Pieper et al. . | |
| 5,156,902 | 10/1992 | Pieper et al. . | |
| 5,213,817 | 5/1993 | Pelley | 425/81.1 |
| 5,248,524 | 9/1993 | Soderlund | 118/308 |
| 5,429,788 | 7/1995 | Ribble et al. | 264/518 |

FOREIGN PATENT DOCUMENTS

| | | | |
|---|---|---|---|
| 588172 | 12/1959 | Canada | 425/83.1 |
| 1134009 | 7/1962 | Germany | 19/296 |

*Primary Examiner*—Steven D. Maki
*Attorney, Agent, or Firm*—Helfgott & Karas

[57] ABSTRACT

A sheet of an absorbent material which, comprises a blend of a fibrous substance and of a granulated substance in which the granulated substance is non-uniformly distributed in the sheet, there being alternating zones of higher and of lower density of said substance along the sheet, is prepared by vacuum depositing (16) a dispersion of the fibrous substance (20) on a moving screen (14) and continuously applying the granulated substance (24) while changing the zone of application in a pendulum-like fashion (34, 36) along the screen.

9 Claims, 2 Drawing Sheets

PREPARATION OF AN ABSORBENT SHEET

FIELD OF THE INVENTION

The present invention concerns means and process for the preparation of a sheet of absorbent material (hereinafter, at times "absorbent sheet"). More specifically, the present invention provides a process and means for the formation of an absorbent sheet comprising a blend of a first, fibrous substance, and a second, granulated substance, wherein the second substance is non-uniformly distributed, there being portions of increased concentration of said second substance, where said second substance is most needed.

A specific application of the present application is in the formation of an absorbent sheet for use as an absorbent medium in disposable diapers.

BACKGROUND OF THE INVENTION

Disposable diapers generally comprise a liquid absorbent layer sandwiched between an external, liquid impervious layer, and an internal, liquid permeable liner. In order to perform its function well, the absorbent layer has to be capable of absorbing large quantities of liquids, many folds larger than its own weight. The main component of the absorbent layer is a fibrous substance such as wood pulp fibers, and in order to improve the liquid absorbance, this layer is supplemented with granules of super absorbent polymers (SAP) which typically constitute about 17–20% of the absorbent layer. SAP is capable of absorbing about 35–40 times its weight in liquid whereas wood pulp fibers are capable of absorbing only about 7 times their weight in liquid. However, SAP, is an expensive material and costs about three times more than wood pulp fibers.

Good liquid absorbance is most important in the front half of the diaper at the area coming in contact with the child's genitals and crotch region. Thus, in view of its high price tag it would have been desirable to have the bulk of the SAP in a diaper in the front half and only a small part of the SAP in the rear half of the diaper. A very desirable ratio between the amount of SAP in the front and in the rear half of the diaper would be about 8:2, i.e. 80% of the SAP in the front half of the diaper and only 20% in the rear half. However, none of the methods available to date in preparing a disposal diaper allows such a distribution of SAP.

The absorbent material of disposable diapers is typically formed as a continuous sheet, which is then sandwiched between the liquid impervious layer on the one hand and the liquid permeable liner on the other hand and cut according to the desired shape. The absorbent sheet is typically produced in a vacuum chamber having a moving screen at its bottom through which the vacuum is applied. Fibers are introduced into this chamber by a stream of air and are then deposited on the screen. The moving screen is typically a foraminous belt on which a continuous sheet of absorbent material is formed; or a rotating drum having shaped depression in which the fibres are deposited, whereby the formed sheet assumes some of the shape characteristics of the subsequently formed disposable diapers. SAP is discharged from a pipe situated above the belt in the chamber and thus applies the SAP into the forming blend of material which forms the sheet. In accordance with known means the SAP was either continuously applied, in which case it became evenly distributed along the formed sheet, and eventually evenly distributed in the produced disposable diapers, or alternatively, the discharge pipe was provided with an intricate and very expensive valve mechanism which allowed the controlled intermittent discharge of SAP only on portions which eventually formed the front half of the disposable diaper.

None of these SAP application means enables to obtain about an 8:2 distribution ratio mentioned above.

It is an object of the present invention to provide novel means for the preparation of an absorbent sheet comprising a blend of two substances, one being a fibrous substance and the other being a particulate substance, in which sheet, the second substance is unevenly distributed.

A particular object of the present invention is to provide means for the preparation of an absorbent sheet for use in disposable diapers in which SAP is located predominantly in the front half.

Various other objects of the invention will be eleviated in the following description and claims.

SUMMARY OF THE INVENTION

The present invention provides a process for the manufacture of a sheet of an absorbent material, the sheet comprising a blend of a first, fibrous substance, and of a second, granulated substance, said second substance being non-uniformly distributed in said sheet, there being alternating zones of higher and of lower density of said second substance along said sheet, said process comprising:

introducing a dispersion of said first substance into a vacuum chamber having a continuous moving porous screen at its bottom, the vacuum in the chamber being applied through said screen, whereby said first substance is being deposited on said screen, and continuously discharging said second substance and depositing it onto an area of said screen from a discharge opening of a discharge means, said discharge means being adapted to cyclically reciprocate the: zone of deposition of the second substance on the screen between two points on a line parallel to the direction of movement of the screen; whereby zones of higher and of lower density of said second substance along said sheet are formed, two zones of equal density being distanced from one another by a distance equal to the distance travelled by the belt during one cycle of reciprocation of said discharge means.

In accordance with a second aspect, the present invention provides an apparatus for the manufacture of a continuous sheet of an absorbent material, the sheet comprising a blend of a first fibrous substance and of a second, granulated substance, said second substance being non-uniformly distributed, there being alternating zones of higher and of lower density of said second substance along said sheet, said apparatus comprising:

a vacuum chamber having a foraminous screen at its bottom and capable of moving at a constant speed driving the sheet deposited thereon through and out of said chamber, and having vacuum forming means adapted to form a vacuum through said screen;

means for introducing said first substance into said chamber in a dispersed form; and discharge means for said second substance having a discharge opening adapted to continuously discharge said second substance and depositing it onto an area of said screen, and being further adapted to cyclically reciprocate the zone of deposition of the second substance on the belt between two points on a line parallel to the direction of movement of the screen.

In accordance with one embodiment of the invention, in a first half of the cycle the area of deposition moves at the same direction and at an average speed being essentially the same as that of the belt.

For many applications, e.g. in the case of absorbent sheets for use in disposable diapers, the second substance should have a higher concentration along the midline of the formed sheet and a lower concentration at peripheral portions of the sheet and the discharge opening is thus preferably adapted to deposit said second substance on an area on the sheet's midline.

In accordance with the present invention, the density of the second substance in the formed sheet follows a longitudinal cyclical distribution pattern, there being portions having a relatively high concentration of said second substance, these being the portions on which the second substance is deposited during the first half of the cycles; other portions in between having a relatively low concentration of said substance, these being the portions on which said second substance is deposited during the second half of said cycle.

In accordance with one embodiment of the present invention, said discharge means is an elastic pipe, having an opening at its bottom end which opening is situated above the belt, said bottom end being connected to driving means adapted to reciprocate said bottom end between a first and a second position, whereby the zone of deposition of said second substance reciprocate between the two points on said line.

Suitably, said driving means consist of a driving wheel connected to the bottom end of the pipe by means of a connecting rod, whereby rotation of said wheel causes reciprocation of the pipe's bottom end. The rotation of the driving wheel is typically coupled to and synchronized with the screen's movement.

A specific embodiment of the present invention concerns the preparation of an absorbent sheet intended to be used as the absorbent layer of a disposable diaper. In such a case, the first substance will typically be wood pulp fibers and the second substance will typically be SAP. As will be appreciated by the artisan, the distance between zones of equal density in sheets intended to be used as the absorbent layer of disposable diapers, is about equal to the diaper's length. Such a sheet is cut at a later stage of manufacture in a manner so that a zone of high concentration of said second substance will be the front half of the diaper.

In the following the invention will be illustrated with reference to a specific embodiment concerned with the preparation of an absorbent sheet for use in the preparation of disposable diapers. It will no doubt be appreciated by the artisan that the invention is not limited to this specific embodiment.

DESCRIPTION OF A SPECIFIC EMBODIMENT

Figure 1:
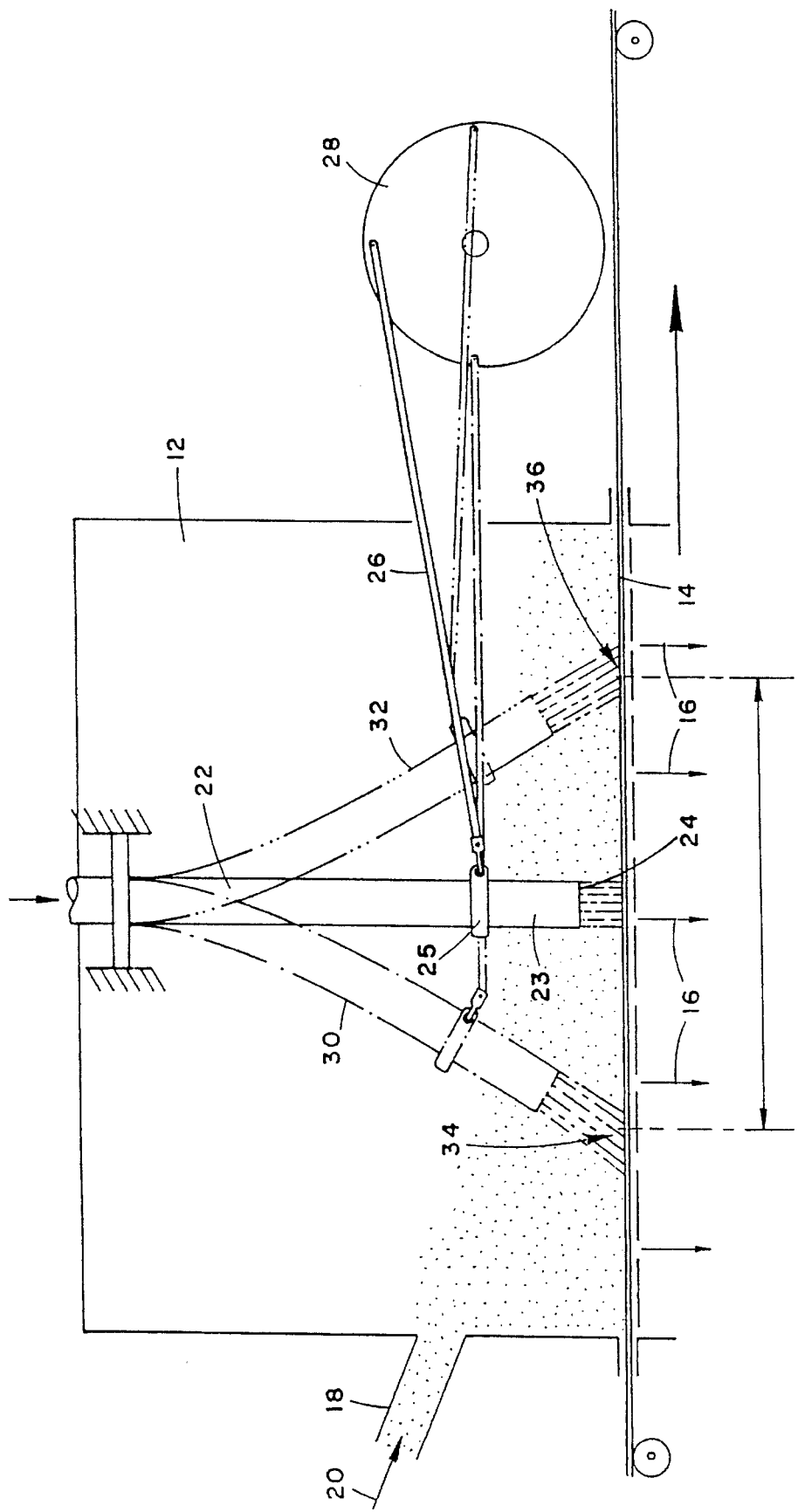
FIG. 1 is a schematical representation of an apparatus of the invention.

Reference is first being made to FIG. 1 showing apparatus for the preparation of an absorbent sheet for disposable diapers. The apparatus shown schematically in FIG. 1 comprises a chamber 12 having in its bottom a continuously moving foraminous belt 14. Vacuum in the chamber is formed through the belt, represented schematically by arrows 16, by appropriate vacuum forming means (not shown) known per se. The vacuum chamber 12 has an inlet 18 through which a dispersed fibrous substance such as wood pulp fibers is introduced, typically by the use of pressurized air represented schematically by arrow 20. As a result of the combined dispersion action of the pressurized air 20 and vacuum formed through belt 14, the fibers are being uniformly deposited on belt 14.

In chamber 12 there is also an elastic discharge pipe 22, adapted to discharge a granulated substance, such as SAP on the midline of the belt 14. Pipe 22 has a discharge opening 24 situated a short distance above belt 14. The bottom end 23 of pipe 22 is fitted with a clasp member 25 articulated to a rod 26 pivotly connected to the periphery of driving wheel 28. Owing to the rotation of wheel 28, the pipe assumes a cyclical reciprocating, pendulum-like motion in a line parallel to the direction of movement of the belt between a first position represented by a singly dotted line 30 and a second position represented by a triply dotted line 32. In the first position, the SAP discharged from pipe 22 is deposited on a first zone 34 and in the second position at zone 36.

In the first part of the cycle, when the pipe moves between first position 30 to the second position 32, the area of deposition advances from zone 34 to zone 36 at an average speech being about the same as that of the belt, i.e. the SAP is deposited on about the same portion of the forming sheet, and in the second half of the cycle the pipe moves in the counter direction. The cycle time of the pipe's reciprocating movement is the same as the time the belt travels a distance equal to the length of the formed sheet intended for a single diaper. Although the cycle time is constant, the distance travelled by the bottom end of the pipe can be changed by changing the position of clasp member 25.

Figure 2:
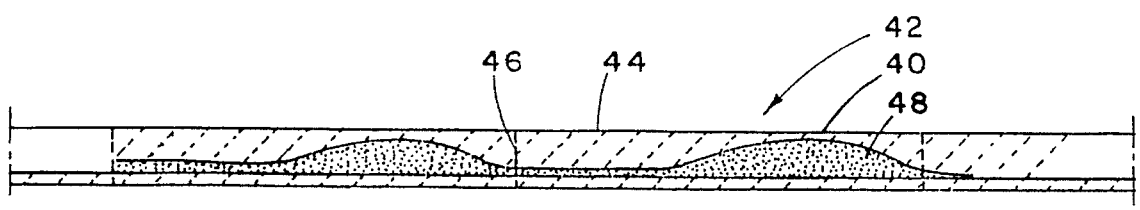
FIG. 2 shows a cross-sectional view through a sheet formed in the apparatus of FIG. 1.

In the specific embodiment shown in FIG. 1, in which the distance between zone 34 and 36 is equal to about half a diaper length, the distribution of SAP in the formed sheet assumes a profile similar to that shown in FIG. 2 in which about 80% of the SAP 48 is concentrated in the first half 40 of each repeating unit 42 and only about 20% is concentrated in the second half 44.

For the production of the disposable diapers, the formed sheet are lined on one side with a liquid impervious layer (not shown) and on the other side with a liquid permeable liner (also not shown) and then formed into a disposable diaper by combining the three layers and then cutting to form the diapers.

Figure 3:
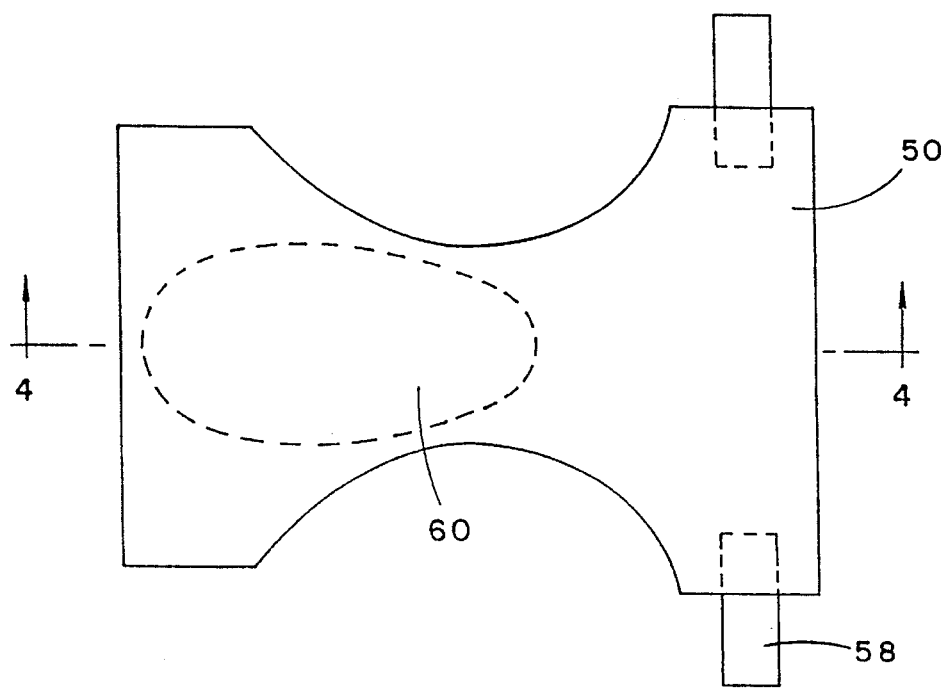
FIG. 3 shows a view from above of a disposable diaper containing an absorbent layer prepared in accordance with the invention.
Figure 4:
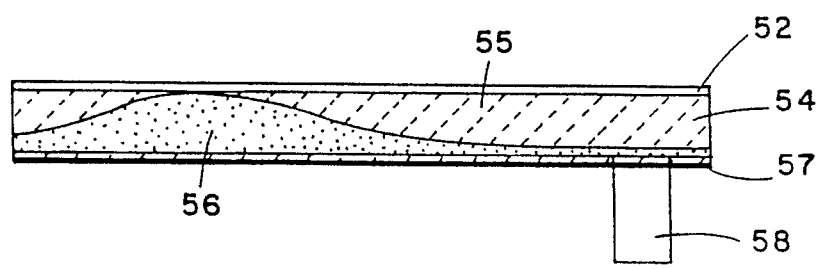
FIG. 4 is a schematical representation of a cross-section through lines 4—4 in FIG. 3.

A disposable diaper is shown in FIG. 3 and a schematical longitudinal cross-sectional view of the diaper is shown in FIG. 4. The diaper 50 has an internal liquid permeable liner 52, an intermediate absorbent layer 54 and an external liquid impervious layer 56 fitted with adhesive fastening strips 58. The absorbent layer 64 consists of a fibrous substance, e.g. wood pump 55 and SAP 56. As can be seen, the SAP 56 in the absorbent layer is unevenly distributed and concentrated mainly in the front half of the diaper in the portion 60 marked by a dotted line. The increased concentration of the SAP in the mid line of the diaper versus the periphery is in view of the fact that the discharge pipe is situated above the mid line of the formed felt-like sheet.

In the above embodiment, the sheet is formed on a foraminous belt. However, it will no doubt be appreciated by the artisan that the invention may be practiced also where the sheet of absorbent material is formed by a process known as "drum forming". Such a process utilizes a rotating foraminous drum, having typically foraminous depressions in which the sheet assumes some of the shape characteristics it will eventually have in the disposable diaper.

I claim:

1. A process for the manufacture of a continuous sheet of extended length of an absorbent material, the sheet comprising a blend of a fibrous substance and of a granulated substance, the sheet having alternating zones of higher density of granulated substance and lower density of granulated substance along said length, the process comprising the steps of:

(a) introducing a dispersion of the fibrous substance into a vacuum chamber having a foraminous screen, the screen moving in a first direction;

(b) providing a vacuum through the screen so as to deposit the fibrous substance onto the screen;

(c) continuously discharging the granulated substance through an opening at an end of a discharge means located above the screen and onto the moving screen; and (d) cyclically reciprocating the end of the discharge means between a first position and a second position so that in a first half of a cycle, the opening moves from the first position to the second position in the first direction so as to form a zone of higher density of granulated substance in said sheet and in a second half of said cycle, the opening moves from the second position to the first position in a second direction, the second direction being opposite of the first direction, so as to form a zone of lower density of granulated substance in said sheet.

2. A process as in claim 1, wherein said discharge means discharges the granulated substance along a midline of the screen.

3. A process as in claim 1, wherein said opening is located at a lower free end of the discharge means and said discharge means is an elastic pipe.

4. A process as in claim 1, wherein in the first half of said cycle the area of deposition of the granulated substance moves in the first direction and at an average speed which is essentially the same as that of the screen.

5. A process as in claim 1, wherein the fibrous substance comprises wood pulp fibers and the granulated substance comprises super absorbent polymer.

6. An apparatus for the manufacture of a continuous sheet of an absorbent material, the sheet comprising a blend of a fibrous substance and a granulated substance, the sheet being of extended length and having alternating zones of higher density of granulated substance and lower density of granulated substance along said length, the apparatus comprising:

(a) a vacuum chamber having an inlet for introducing a dispersion of the fibrous substance into said chamber;

(b) a foraminous screen located in said vacuum chamber, said screen being adapt to move in a first direction;

(c) vacuum forming means for providing a vacuum through said screen for depositing the fibrous substance onto said screen;

(d) a discharge means having an opening at an end thereof above said screen for continuously discharging granulated substance onto said screen; and (e) a driving mechanism for cyclically reciprocating said end of said discharge means between a first position and a second position such that in a first half of a cycle, said opening is moved from said first position to said second position in said first direction so as to form a zone of higher density of granulated substance in said sheet and in a second half of said cycle, said opening is moved from said second position to said first position in a second direction, said second direction being opposite of said first direction so as to form a zone of lower density of said granulated substance in said sheet.

7. An apparatus as in claim 6, wherein said discharge means is located above the screen such that the discharge means discharges the granulated substance along a midline of said screen.

8. An apparatus as in claim 6, wherein said opening is at a lower end of the discharge means and said discharge means is an elastic pipe.

9. An apparatus as in claim 6, wherein said driving mechanism moves said end of said discharge means such that in a first half of a cycle the area of deposition of the granulated substance moves in the first direction and at an average speed which is essentially the same as that of the screen.

* * * * *